(12) United States Patent
Brunet et al.

(10) Patent No.: US 7,569,213 B2
(45) Date of Patent: Aug. 4, 2009

(54) IMMUNOTHERAPEUTIC AGENT

(75) Inventors: Laura Rosa Brunet, Essex (GB); Graham Rook, London (GB)

(73) Assignee: Stanford Rook Limited, London (GB)

( * ) Notice: Subject to any disclaimer, the term of this patent is extended or adjusted under 35 U.S.C. 154(b) by 0 days.

(21) Appl. No.: 11/667,770

(22) PCT Filed: Nov. 22, 2005

(86) PCT No.: PCT/GB2005/004478

§ 371 (c)(1), (2), (4) Date: May 15, 2007

(87) PCT Pub. No.: WO2006/054110

PCT Pub. Date: May 26, 2006

(65) Prior Publication Data

US 2008/0004341 A1   Jan. 3, 2008

(30) Foreign Application Priority Data

Nov. 22, 2004 (GB) ................................. 0425658.2

(51) Int. Cl.
*A61K 31/74* (2006.01)
*A23D 9/00* (2006.01)
(52) U.S. Cl. ................. 424/78.05; 424/78.02; 554/227; 554/223; 554/224; 514/547
(58) Field of Classification Search ............... 424/78.02, 424/78.03, 78.05; 554/227, 223, 224
See application file for complete search history.

(56) References Cited

U.S. PATENT DOCUMENTS

| | | | |
|---|---|---|---|
| 3,988,446 | A | 10/1976 | Paris et al. |
| 4,178,373 | A | 12/1979 | Foxx et al. |
| 5,709,855 | A | 1/1998 | Bockow et al. |
| 5,807,572 | A | 9/1998 | Kim et al. |
| 5,866,703 | A | 2/1999 | Horrobin et al. |
| 6,479,070 | B1 | 11/2002 | Cain et al. |
| 6,589,520 | B1 * | 7/2003 | Hoppe et al. ............. 424/78.05 |

FOREIGN PATENT DOCUMENTS

| | | | |
|---|---|---|---|
| DE | 3314786 A1 * | 10/1984 | |
| EP | 0 289 204 | 11/1988 | |
| EP | 0 311 091 | 4/1989 | |
| EP | 0 491 076 | 6/1992 | |
| GB | 2 300 807 | 11/1996 | |
| JP | 63-088123 | 4/1988 | |

(Continued)

OTHER PUBLICATIONS

Barnes, P., New treatments for chronic obstructive plumanory disease, 2003, Ann 1st Super Sanita, vol. 39, No. 4, pp. 573-582.*

(Continued)

*Primary Examiner*—Porfirio Nazario-Gonzalez
*Assistant Examiner*—Yate' K Cutliff
(74) *Attorney, Agent, or Firm*—Nixon & Vanderhye P.C.

(57) ABSTRACT

The invention relates to a compound which is an ester of 1,2,3-propanetriol with one or more $C_{11}$ to $C_{24}$ fatty acids, wherein at least one fatty acid has at least one double bond. The compound is useful in the treatment of chronic inflammatory disorders.

74 Claims, 5 Drawing Sheets

FOREIGN PATENT DOCUMENTS

| | | | |
|---|---|---|---|
| JP | 02129113 A | * | 5/1990 |
| WO | 92/01450 | | 2/1992 |
| WO | 93/00326 | | 1/1993 |
| WO | 93/21912 | | 11/1993 |
| WO | 98/56371 | | 12/1998 |
| WO | 99/45916 | | 9/1999 |
| WO | 2004/000333 | | 12/2003 |

OTHER PUBLICATIONS

Knothe, G. et al, Evaluation of C-NMR signals of the unsaturated carbons of triacylglycerols, 1995, Chemistry and Physics of Lipids, vol. 77, pp. 187-191.*

Lassmann, H., Recent neuropathological finds in MS-implications for diagnosis and therapy, Sep. 2004, Journal of Neurology, vol. 251, supp. 4, pp. 1432-1459.*

* cited by examiner

IMMUNOTHERAPEUTIC AGENT

This application is the U.S. national phase of International Application No. PCT/GB2005/004478 filed 22 Nov. 2005, which designated the U.S. and claims priority to GB 0425658.2 filed 22 Nov. 2004, the entire contents of each of which are hereby incorporated by reference.

The invention provides a compound which is an ester of 1,2,3-propanetriol with one or more $C_{11}$ to $C_{24}$ fatty acids, wherein at least one fatty acid has at least one double bond. The compound may be used in the treatment of chronic inflammatory disorders.

BACKGROUND OF THE INVENTION

The immune system reacts to challenge in a very selective and highly defined manner. T-helper lymphocytes play a central role and by either favouring T helper 1 (Th1) or Th2 development, they orchestrate immunological responses through the release of specific cytokines. This dichotomy is particularly evident following exposure to intracellular bacteria or viruses when Th1 responses predominate and mediate protection, and during helminth infestations when Th2 responses are preferentially developed (Abbas A K et al., Nature (1996), 387, 787-793; Mosmann T R et al., Imm Rev (1991) 123, 209-229 ). A Th1 response is accompanied by production of interleukin 2 (IL-2) and gamma interferon (IFN-γ). These cytokines drive specific antibody subclasses and enhance cellular immune responses through activation of macrophages and generation of CD8 cytotoxic T-lymphocytes. A Th2 response is characterized by an increase in IL-4, IL-5 and IL-13. These cytokines stimulate increased IgE levels, induce eosinophilia and mucus secretion and are associated with allergic inflammation.

It was initially thought that Th1 and Th2 responses effectively regulate each other (Mosmann T R et al., Imm Res (1991) 10, 183-188). However, evidence from epidemiological studies and from a number of in vivo models has cast doubt on the mutual antagonisms of Th1 and Th2 cells (Rook G A et al., Immunol Today (2000), 21, 508-508; Rook et al. Springer Sem Immunopathol. (2004) 25: 237-255). Th1 effector cells rather than successfully switching off Th2-mediated allergic reactions in vivo may contribute additional immunopathology (Hansen G et al., J Clin Invest (1999), 103, 175-183). In a recent human clinical trial, administration of IL-12 to asthmatics reduced the magnitude of the Th2 response as suggested by the fall in eosinophil count, but failed to decrease the late asthmatic response to allergen (Bryan S A et al., Lancet (2000), 356, 2149-2153). In Th1-mediated conditions such as experimental allergic encephalitis (EAE) (Lafaille J J et al., J Exp Med (1997), 186, 307-312) and diabetes in non-obese diabetic (NOD) mice (Pakala S V et al., J Exp Med (1997), 186, 299-306) a superimposed Th2 response, rather than relieving inflammation, precipitates pathology (Lafaille et al., 1997; Pakala et al., 1997). Moreover, switching the immune response from predominantly Th1 to predominantly Th2 may merely result in a different but equally dangerous disease (Genain C P et al., Science (1996), 274, 2054-2057). In a treatment trial of human multiple sclerosis with a humanised anti-CD52 mAb that resulted in a partial switch from Th1 to Th2, the disease changed in nature without overt improvements, and autoimmune thyroid disease appeared, superimposed upon the modified disease (Coles A J et al., Lancet (1999), 354, 1691-1695).

On account of these discrepancies, research has focussed on identifying the cells responsible for successfully regulating both Th1 and Th2 responses, under conditions where these responses were no longer necessary. A number of candidates have been suggested including specific subsets of dendritic cells (Chan, C et al., Transplant Proc (2004), 36, 561S-569S), regulatory macrophages Mochida-Nishimura, K et al., *Cell Immunol* (2001), 214, 81-88) and several subsets of regulatory T lymphocytes ($T_{reg}$) (Read, S and Powrie, F, Curr Opin Imnunol (2001), 13, 644-649). The latter group is particularly intriguing. Mechanisms of immunoregulation are characterized by mRNA expression and production of interleukin 10 (IL-10) and/or transforming growth factor beta (TGF-β) (Fukaura H et al., J Clin Invest (1996), 98, 70-77; Read and Powrie, 2001, Groux et al., Nature (1997) 389: 737-742). Production of these cytokines, and in particular IL-10 which is considered a hallmark of immunoregulation, along with expression of inhibitory signals such as CTLA-4 mediates immunoregulation by preventing Th1 and Th2 cell proliferation (Read and Powrie, 2001). In addition they maintain tolerance in the periphery by controlling unnecessary immune responses to common antigens, allergens or self (Cottrez et al, J Immunol (2000), 165, 4848-4853; Read and Powrie, 2001).

Pathogenesis in a number of human diseases, including allergy, intestinal bowel disease and some autoimmune conditions is a direct result of faulty immunoregulation. For example, this has become evident following the study of a rare X-linked genetic disorder of man, known as IPEX (immune dysregulation, polyendocrinopathy, enteropathy, X-linked syndrome) or as XLAAD (X-linked autoimmunity-allergic dysregulation syndrome), and an equivalent syndrome in mutant mice called "Scurfy". In Scurfy mice (Brunkow, M et al., Nat Genet (2001), 27, 68-73) and in patients with IPEX/XLAAD, mutations in the transcription factor Foxp3 (Wildin, R S et al., Nat Genet (2001), 27, 18-20) impair development of $T_{reg}$ (Fontenot, J D et al., 2003; Hori, S et al., 2003). The pathology, at times fatal, has components of allergy, autoimmunity and inflammatory bowel disease (IBD). These are three major classes of chronic inflammatory disorders, which affect a large percentage of the human population.

Allergies, which have increased dramatically in the last few decades, are a result of excessive immune responses to aeroallergens, or allergens on skin or in the gut. The immediate explosive Th2-mediated response to allergen that causes clinical allergies originally evolved to respond to helminths. Disease is characterized by increased eosinophilia, IgE and mucus secretion to minute concentrations of allergens. These inappropriate responses can be controlled by IL-10-secreting $T_{reg}$ (Cottrez F et al., 2000). Therefore it is now accepted that immunoregulatory mechanisms are required to switch off allergic responses in animals and in man. Successful immunotherapy with high dose allergen works in some patients, and is accompanied by increased production of IL-10, and increased activity of immunoregulatory mechanisms (Francis J N et al., J Allergy Clin Immunol (2003), 111, 1255-1261; Nouri-Aria K T et al., J Allergy Clin Immunol (2002), 109, S171 (abs 105)).

Autoimmune diseases occur as a result of the host's immune system attacking its own tissues. It is a failure of regulation of the inherent anti-self capacity of the T cell repertoire selected in the thymus. Several of the most disabling autoimmune diseases of man are Th1-mediated and are increasing in frequency. Examples include multiple sclerosis and type 1 diabetes. Others, such as systemic lupus erythematosus and systemic sclerosis, are largely mediated by Th2 cells. A wide variety of organ-specific autoimmune disorders can be controlled by $T_{reg}$ expressing TGF-β and IL-10 mRNA (Seddon B and Mason D, Immunol Today (2000), 21, 95-99). They can inhibit both Th1-mediated (Cavani A et al., J Invest Dermatol (2000), 114, 295-302) and Th2-mediated autoimmunity (Bridoux F et al., J Exp Med (1997), 185, 1769-1775). Under experimental conditions, $T_{reg}$ engineered to secrete TGF-β downregulates both Th2- and Th1-mediated responses (Thorbecke G J et al., Cytokine Growth Factor Rev (2000), 11, 89-96).

Current evidence suggests that IBD (Crohn's disease and ulcerative colitis) is a result of a failure of immunoregulatory mechanisms to inhibit immune responses to gut content such as food or microbes (Boismenu R and Chen Y, J Leukoc Biol (2000), 67, 267-278). For instance IBD occurs in mice that lack IL-10 (gene knockout) and also in mice with severe combined immunodeficiency (SCID) that receive effector T cells (CD4+CD45RB$^{high}$) without the appropriate $T_{reg}$ (CD4+CD45RB$^{low}$) (reviewed in (Asseman C and Powrie F, Gut (1998), 42, 157-158)). There is good evidence that $T_{reg}$ stop the inflammatory process in IBD through IL-10 (Singh B et al., Immunol Rev (2001), 182, 190-200). This cytokine is undergoing clinical trials as a treatment for IBD in animal models (Van Montfrans C et al., Gastroenterology (2002), 123, 1865-1876) and man (Braat H et al., Expert Opin Biol Ther (2003), 3, 725-731). Other members of the IL-10 family of cytokines (including IL-19, IL-20, IL-22, IL-24, IL-26, IL-28 and IL-29) might also be involved.

The inventors believe that in the rich developed parts of the world, there has been a large and simultaneous increase in the same three groups of chronic inflammatory disorders; 1) the allergies (Bach, J F, N Engl J Med (2002), 347, 911-920), 2) the inflammatory bowel diseases (for example Crohn's disease and ulcerative colitis) (Weinstock J V et al., Gut (2004) 53, 7-9), and 3) autoimmunity (for example, type 1 diabetes and multiple sclerosis) (Bach, 2002). The increases in allergies and Type 1 diabetes are precisely correlated both within Europe and outside Europe (Stene L C and Nafstad P (2001), Lancet 357, 607). The increases are occurring simultaneously whether the disease is mediated by Th1 cells (type 1 diabetes, multiple sclerosis, Crohn's disease (Elliott D E et al., Faseb J (2000), 14, 1848-1855) or Th2 cells (allergies). There is now general agreement that the underlying problem is the inefficient activation of immunoregulatory mechanisms in the developed countries. Impairment of $T_{reg}$ functions such as production of IL-10 may be to blame. This may be attributable to changing exposure to certain microorganisms (Rook G A et al., Springer Semin Immunopathol (2004), 25, 237-255).

SUMMARY OF THE INVENTION

The present inventors have found that a particular group of fatty acids and mono-, di- and tri-esters of the fatty acid and 1,2,3-propanetriol are effective in the treatment of chronic inflammatory disorders.

The invention provides a compound which is an ester of 1,2,3-propanetriol with one or more $C_{11}$ to $C_{24}$ fatty acids, wherein at least one fatty acid has at least one double bond. The compound will have the general formula:

where $R_1$, $R_2$ and $R_3$ may be the same or different and are either H or a residue of a $C_{11}$ to $C_{24}$ fatty acid, wherein at least one of $R_1$, $R_2$ and $R_3$ is other than H, and at least one of the fatty acids has at least one double bond.

The fatty acid is suitably a $C_{11}$ to $C_{24}$ fatty acid, e.g. $C_{11}$, $C_{12}$, $C_{14}$, $C_{16}$, $C_{18}$, $C_{20}$, $C_{22}$ or $C_{24}$, preferably a $C_{11}$ to $C_{20}$ fatty acid, more preferably a $C_{11}$ to $C_{16}$ fatty acid, particularly a $C_{11}$ or $C_{12}$ fatty acid. The fatty acid preferably has one double bond in the molecule. The double bond of the fatty acid suitably occurs at position C11-C11. The double bond may be cis or trans, and is preferably cis.

The compound is either a mono-, di- or tri-ester, preferably a tri-ester. When the compound is a mono-ester, esterification may occur at the 1- or 2-position, preferably at the 1-position. When the ester is a di-ester, esterification may occur at the 1- and 2-positions, or the 1- and 3-positions, preferably at the 1- and 3-positions.

The compound of the invention is preferably a tri-ester of 1,2,3-propanetriol and hexadecenoic acid (10Z).

The invention also provides the use of the compounds as defined above in the preparation of a medicament for the treatment of chronic inflammatory disorders. The inventors have found that the free fatty acid alone is also effective and the invention further provides the use of a $C_{11-24}$ fatty acid having at least one C10-11 double bond in the preparation of a medicament for the treatment of a chronic inflammatory disorder. The fatty acid is preferably $C_{11-16}$, and more preferably is hexadecenoic acid (10Z).

The chronic inflammatory disorders may include allergic disorders, autoimmune diseases and inflammatory bowel diseases.

Examples of allergic disorders include asthma, eczema, hayfever, allergic rhinitis, atopic dermatitis, food allergy. Examples of an autoimmune disease may include multiple sclerosis, type I diabetes, psoriasis, rheumatoid arthritis, systemic sclerosis and systemic lupus erythematosus. Examples of an inflammatory bowel disease (IBD) may include Crohn's disease and ulcerative colitis.

The compounds of the invention may be made by a process which is defined in Example 1 by a schematic illustration.

Throughout the present specification and the accompanying claims the words "comprise" and "include" and variations such as "comprises", "comprising", "includes" and "including" are to be interpreted inclusively. That is, these words are intended to convey the possible inclusion of other elements or integers not specifically recited, where the context allows.

The compounds of the invention or the free fatty acids as defined above may be used in the preparation of a medicament. The medicament may further comprise standard pharmaceutically acceptable carriers and/or excipients as is routine in the pharmaceutical art. For example, the compound of the invention or the defined free fatty acid may be put into suspension in, for example, a physiological buffer, isotonic saline or water by physical disruption such as ultrasound. Alternatively it may be put into suspension by ultrasound in the presence of a stable carrier protein, for example lipid-free human serum albumin, to which the lipid and/or glycolipid will bind, providing a stable solution.

Alternatively the compounds of the invention or the free fatty acids as defined above may be formulated as slow release pellets following combination with a suitable carrier molecule, for example cholesterol. A suitable carbohydrate that is linked to a lipid or glycolipid may be formulated in the same way as a lipid and/or glycolipid. A suitable carbohydrate not linked to a lipid or glycolipid may be dissolved in, for example, physiological saline or water for injection. The exact nature of a formulation will depend upon several factors including the particular substance to be administered and the desired route of administration. Suitable types of formulation are fully described in Remington's Pharmaceutical Sciences, Mack Publishing Company, Eastern Pennsylvania, 17$^{th}$ Ed. 1985, the disclosure of which is included herein of its entirety by way of reference.

The pharmaceutical composition comprising compounds of the invention or the free fatty acids as defined above may also contain further ingredients such as adjuvants, preservatives, stabilisers etc. It may further comprise other therapeutic agents. It may be supplied in sterile and pyrogen free form, for example as an injectable liquid; in sterile freeze-dried form which is reconstituted prior to use; or as sterile slow-release pellets. The pharmaceutical composition may be supplied as an isotonic liquid. It may be supplied in unit dosage form.

The medicament comprising the compounds of the invention or the free fatty acids as defined above may be administered by enteral or parenteral routes such as via the oral, buccal, anal or topical route, by subcutaneous, intradermal, intravenous, intramuscular or intradermal injection, by aerosol into the airways, or by other appropriate administration routes. Particularly preferred routes of administration are the oral route or by subcutaneous or intramuscular injection, intradermal and topical. A physician will be able to determine the required route of administration for any particular patient.

A therapeutically effective amount of the compound of the invention or the free fatty acids as defined above is administered to a patient. The dose may be determined according to various parameters, especially according to the substance used; the age, weight and condition of the patient to be treated; the route of administration; and the required regimen. A physician will be able to determine the required route of administration and dosage for any particular patient. Multiple doses may be given. A typical individual dose is from about 0.005 to 1.0 mg/kg, preferably from about 0.01 to 0.5 mg/kg, more preferably from about 0.03 to 0.3 mg/kg, according to the activity of the specific lipid, glycolipid and/or carbohydrate preparation, the age, weight and condition of the subject to be treated, the type and severity of the allergy and the frequency and route of administration.

The invention is illustrated by the attached Figures.

The invention will be described with reference to the following Examples, which are intended to be illustrative only and not limiting.

EXAMPLES

The following models were used in testing:

Allergic Pulmonary Inflammation Model

In order to evaluate the compounds of the invention, the inventors have developed an experimental model of allergic pulmonary inflammation. This model is used below to evaluate the effect of the compounds of the invention and to carry out comparative tests.

Protocols in Use

Two protocols to test treatment efficacy have been optimized by the inventors. The prevention protocol is designed to determine the ability of treatment to prevent the development of symptoms of allergic pulmonary inflammation in subsequently sensitized mice. The therapeutic protocol is designed to determine the ability of treatment to cure symptoms of allergic pulmonary inflammation in sensitized mice.

In the prevention protocol Balb/c female mice (7-8 weeks of age, 17-20 g in weight) are treated with saline or buffer—0.001% FFA albumin in saline (as positive control) or lipid fractions of mycobacteria (taken form the sample deposited at the National Collection of Type Cultures under deposit number NCTC 11659). Three weeks after treatment all mice are sensitized intraperitoneally with 10 µg ovalbumin (OVA) and Alum (a 100 µl preparation of Alum supplied by Serva-Alu-Gel-S suspension). Sensitization is repeated after twelve days. On day 19, mice are intratracheally challenged with OVA (0.5 µg in 50 µl saline). Intratracheal antigenic challenge is repeated two days later. Twenty-four or 48 hours after the last challenge, the experiment is terminated.

In the therapeutic protocol mice are sensitized with OVA and Alum on day 0 and 12. On day 21, mice are treated as appropriate. Mice are resensitized on days 42 and 54. On days 61 and 63, mice are challenged intratracheally with OVA and the experiment terminated 24 or 48 hours later. This therapeutic protocol mirrors more closely the situation in human patients, which have established allergic conditions prior to treatment.

In some experiments, a small number of mice from the positive control group are challenged intratracheally with saline alone to determine the background level of cells infiltrating the lungs of sensitized mice in the absence of an allergic episode (negative control).

Samples Collection

A number of end points are routinely assessed. Mice are bled by cardiac puncture and blood collected for serum analysis. The lungs are lavaged three times with 0.3 ml of sterile RPMI containing Penicillin/Streptomycin. The lavage fluid is collected and recovered cells are counted. Fifty or 100 µl of lavage fluid is used for a cytospin, which is stained (Wright-Giemsa stain), fixed in methanol and used for the morphological identification of specific cell populations of interest (eosinophils, neutrophils and monocytes/macrophages). The remaining fluid is spun down and the supernatant stored for cytokine measurement by ELISA. Spleens are pooled per treatment groups, a single cell suspension of splenocytes is obtained and placed in culture with OVA for specific antigenic stimulation and with anti-CD3 for polyclonal T cell stimulation. Supernatants are collected and stored for cytokine measurement by ELISA.

Example 1

Isolation of Lipids

Wet mycobacterial (NCTC 11659) cells (200 g of paste) were extracted using 440 mL of petroleum ether, 400 mL of methanol, 40 mL 0.3% aqueous sodium chloride overnight with gentle agitation. The mixture was then left to stand and the upper organic petroleum-ether supernatant fraction separated by careful aspiration. The lower aqueous phase was extracted again using petroleum ether (400 mL) as described above. The petroleum-ether extracts were combined and dried to yield the apolar lipids. The lower aqueous phase was then extracted using chloroform/methanol/water (90:100:30; 520 mL) with gentle agitation, overnight. The resulting lipid extract was separated by vacuum filtration and the residual biomass extracted using chloroform/methanol/water (50:100:40; 170 mL) overnight with gentle agitation twice. The three polar lipid extractions were combined and chloroform (290 mL) and 0.3% aqueous sodium chloride (290 mL) added.

The entire mixture was briefly shaken, allowed to settle and the upper phase carefully removed and discarded. The lower organic layer was dried to yield the polar lipids. The polar lipids were re-suspended in a minimum volume of chloroform (20 mL) and added to chilled acetone (1.5 L) and left at 4° C., overnight. The resulting precipitate was separated by centrifugation from the acetone soluble lipids (220 mg) designated 1.4.8, and further fractioned using column chromatography using increasing amounts of methanol in chloroform to afford seven lipidic fractions. These were screened for their immunological potential as described below. While a number of fractions were deemed interesting, fraction, 1.4.8.2 (82 mg) was further analysed. The resulting fraction was deemed pure by thin-layer chromatography (TLC) using chloroform as an eluant following charring with a heat gun after spraying with 5% ethanolic molybdophosphoric acid. Through a combination of NMR experiments, $^1$H, $^{13}$C, 2D COSY and $^1$H/$^{13}$C HMBC NMR and GC-MS analyses the structure of this lipid was completely determined.

Synthesis of TAG

The synthetic route to TAG was based on the method of Besra et al., Chem. Phys. Lipids (1993), 66, 23-34, and is set out in the Schematic Illustration below. The acetylenic carboxylic acid and trimethylsilyl chloride (0.1 eq.) in anhydrous methanol were mixed at room temperature for 12 hours. The reaction was evaporated to dryness to yield the pure carboxylic acid methyl ester product (Scheme 1, Step 1) as confirmed by TLC and 1H/13C-NMR analysis and was used directly in the next step without further purification.

The carboxylic acid methyl ester was dissolved in diethyl ether and two equivalents of lithium aluminium hydride added and the reaction stirred at room temperature for 4 hours. The reaction was quenched with glacial acetic acid and the acetylenic alcohol product (Step 2) extracted with diethyl ether and water. The ethereal layer was recovered and washed with water and then brine, then concentrated to dryness. The product from Step 2 was purified by flash chromatography and characterised by $^1$H/$^{13}$C-NMR.

To a solution of the acetylenic alcohol (product from Step 2) (1 equivalent) in HMPA, n-butyl lithium (2 equivalents) was added at 0° C. under nitrogen over a period of 30 min. The reaction was stirred at 0° C. for 20 min. 1-Iodopentane (1.4 equivalent) added and the reaction mixture was left to warm to ambient temperature and stirred for 20 hours. The reaction was quenched with the addition of saturated aqueous ammonium chloride and the product from Step 3 extracted with diethyl ether.

The product was concentrated and purified by flash column chromatography, monitored by TLC and characterised by 1H/$^{13}$C-NMR. A suspension of Lindlar's catalyst in dry benzene was saturated with hydrogen gas and cooled to 10° C. Then a solution of the product from Step 3 in benzene and quinoline was added under a stream of nitrogen. The reaction mixture was stirred for 1 hour at 10° C. The reaction mixture was filtered, concentrated and the olefinic product (Step 4) was purified by column chromatography using a petroleum ether-ethyl acetate gradient, monitored by TLC and characterised by $^1$H/$^{13}$C-NMR.

A solution of the olefinic product in dichloromethane (1 volume) was added to a stirring solution of pyridinium dichromate (4 equivalents) in dimethylformamide (DMF, 10 volumes). The reaction mixture was stirred for two days at room temperature. Water was added and the resulting acid (Step 5) was extracted into dichloromethane, washed with brine and concentrated. The product was purified by column chromatography and characterised by MS and $^1$H/$^{13}$C-NMR.

The acid was dissolved in dichloromethane/DMF and oxalyl chloride was added and the reaction mixture stirred at room temperature for 1 hour. The reaction mixture was evaporated and the crude acid chloride (Step 6) was used in the next step.

Glycerol (1 equivalent) in pyridine was added to the acid chloride (3.3. equivalents) and the reaction mixture was left to stir overnight. Dichloromethane and water was added to the reaction mixture and the product recovered in the organic layer and concentrated. The synthetic TAG was purified by column chromatography using increasing methanol in chloroform, monitored by TLC and characterised by MS, and $^1$H/$^{13}$C-NMR analyses.

Characteristic $^1$H/$^{13}$C NMR signals included ($^1$H NMR 300 MHz, CDCl$_3$): d=0.58 (t, J=6.6 Hz, 9H), 1.18-1.32 (m, 54H), 1.54-1.62 (m, 6H), 1.92-2.03 (m, 12H), 2.32 (t, J=5.7 Hz, 6H), 4.13 (dd, J=6.6 Hz, J=12.1 Hz, 2H), 4.25 (dd, J=4.6 Hz, J=12.1 Hz, 2H), 5.21-5.28 (m, 1H), 5.29-5.37 (m, 6H); ($^{13}$C NMR 75 MHz, CDCl$_3$): d=13.0, 21.5, 23.8, 26.1, 28.0, 28.2, 28.3, 28.4, 28.7, 30.4, 32.9, 33.1, 61.0, 67.8, 128.7, 128.9, 169.8, 172.2.

Electro-spray mass spectrometry analysis of the synthetic triacylglycerol yielded the sodiated molecular ion at 823.

Scheme 1
Schematic illustration of synthesis of TAG (steps 1-7).

Example 2

The $C_{16}$ cis 11,12-TAG was prepared according to Scheme 1 set out in Example 1. The reaction may be set out as follows:

Example 3

Other TAGs are prepared as follows, using Scheme 1 set out above in Example 1:

-continued

For $C_{14} X = 2$
For $C_{14} X = 4$
For $C_{14} X = 6$

Example 4

Comparison of treatment with preparations of FFA and TAG containing mixed C16 and C18 lipid chains.

Figure 1:
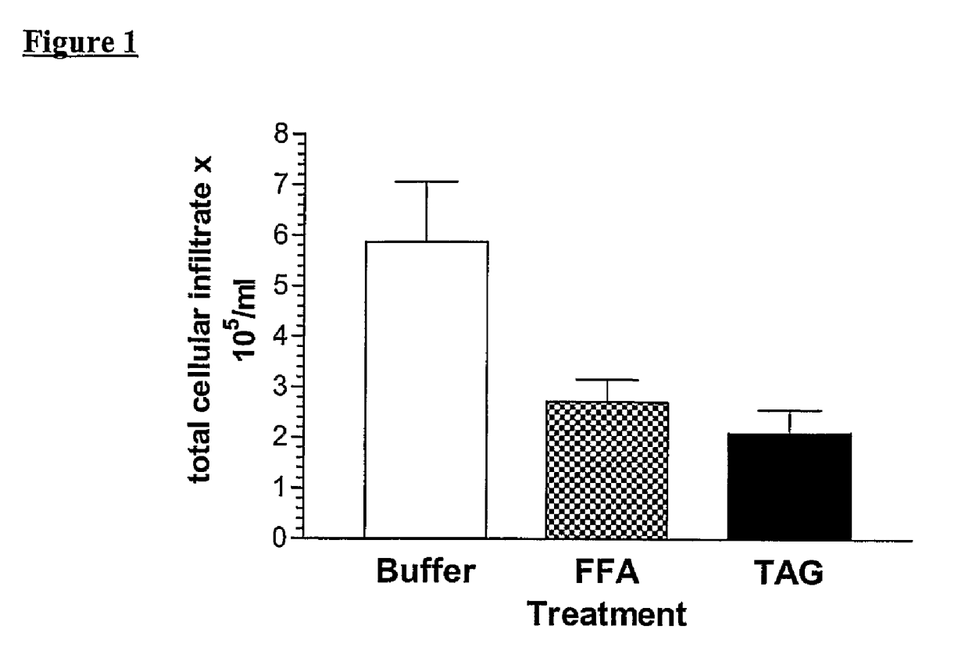
FIG. 1 shows results of total cellular infiltrate following challenge with control, free fatty acid (FFA) and triacylglyseride (TAG) containing mixed C16 and C18 lipid chains.

Following sensitization with ovalbumin and alum, intratracheal challenge of allergic mice with ovalbumin induces a large cellular influx in the lungs as measured by the number of cells recovered in the bronchoalveolar lavage (BAL) fluid. This cellular infiltrate is caused by the allergen challenge, as allergic mice challenged with saline show no symptoms of pulmonary inflammation. We investigated whether treatment with specific lipid preparations is able to decrease the inflammatory infiltrate in the lungs of allergen-challenged allergic mice. We found that treatment with either FFA or TAG preparations containing mixed C16 and C18 lipid chains induces a significant reduction in the total cellular infiltrate compared to mice treated with buffer (FIG. 1). It is clear from the results in FIG. 1 that both FFA and TAG preparations have activity.

Example 5

Comparison of treatment with synthetic compounds SRP312f and SRP312t.

Figure 2A:
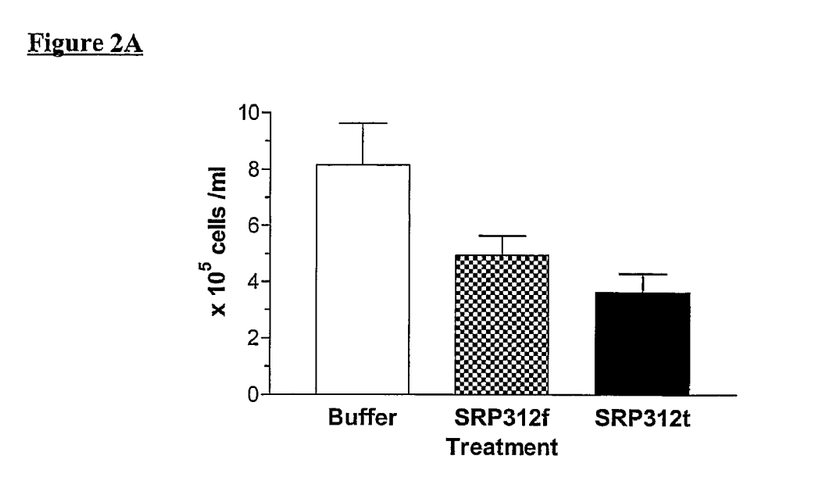
FIG. 2A shows results of total cellular infiltrate following challenge with control, C16:1 10-11 FFA (SRP312f) and C16:1 10-11 TAG (SRP312t).

The FFA and TAG preparations investigated previously (see example 4) contain a peculiar lipid characterized by C16 chains and an unusual double bond at position 10-11. A synthetically produced C16 with this same characteristic as its naturally occurring counterpart was then tested to determine whether it improved symptoms of pulmonary allergic inflammation in a murine model. We compared a C16:1 10-11 FFA (SRP312f) and a C16:1 10-11 TAG (SRP312t). Mice were sensitized with ovalbumin in alum and treated with SRP312f and SRP312t. Allergic mice were then challenged intratracheally with ovalbumin and the ensuing pulmonary inflammation quantified. We found that both SRP312t and to a lesser extent SRP312f reduced the total cellular infiltrate in allergen challenged allergic mice (see FIG. 2A).

Figure 2B:
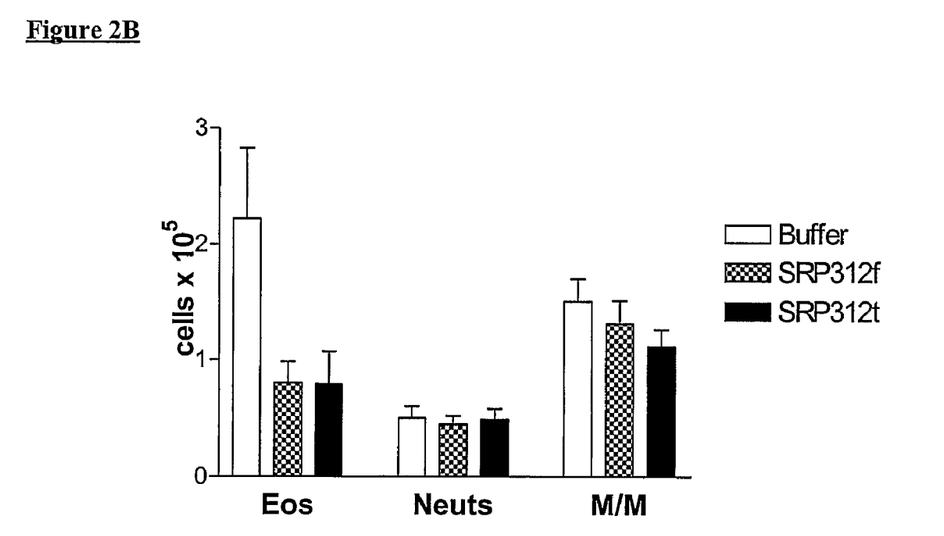
FIG. 2B shows levels of eosinophils, neutrophils and monocytes/macrophages following challenge with control, SRP312f and SRP312t.

Allergic pulmonary inflammation is associated with a large influx of eosinophils, neutrophils, lymphocytes and monocytes/macrophages. We found that mice treated with SRP312f and SRP312t presented a significant reduction in the number of eosinophils recovered in the BAL fluid. The decreased eosinophilia did not result in neutrophilia or in an increase of monocytes or macrophages at the site of inflammation (see FIG. 2B). These results suggested that treatment of allergic mice with SRP312f and SRP312t significantly reduced the severity of the cellular inflammation following allergen challenge.

Figure 2C:
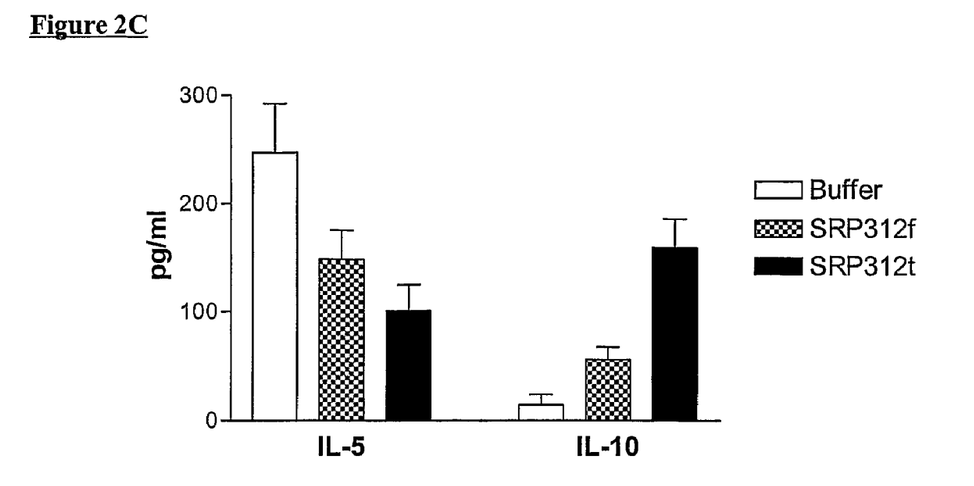
FIG. 2C shows levels of IL-5 and IL-10 in the BAL fluid following challenge with control, SRP312f and SRP312t.

We measured the levels of IL-5 and IL-10 in the BAL fluid to determine the cytokine milieu at the site of inflammation. We found that whereas IL-5 levels were reduced following treatment with SRP312f and SRP312t, IL-10 levels were increased (see FIG. 2C). This suggests a cytokine environment biased towards immunoregulation.

Example 6

Comparison of treatment with different doses of synthetic compound SRP312t.

Figure 3:
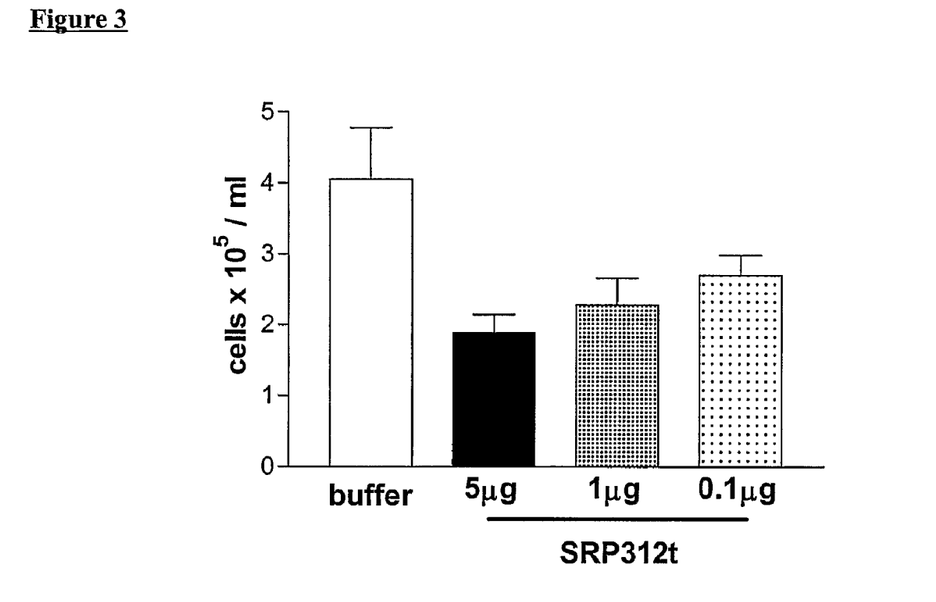
FIG. 3 compares results of total cellular infiltrate on administration of varying doses of SRP312t.

We compared the therapeutic effects of different treatment doses of SRP312t. Mice were sensitized with ovalbumin in alum and treated with 5 µg, 1 µg or 0.1 µg of SRP312t. Allergic mice were then challenged intra-tracheally with ovalbumin and the ensuing pulmonary inflammation quantified. We found that a single dose as low as 1 µg was able to significantly reduce the total cellular infiltrate in the lungs of allergen challenged allergic mice (FIG. 3).

Example 7

Comparison of treatment with different synthetic variants of compound SRP312t.

Chain Length

Figure 4A:
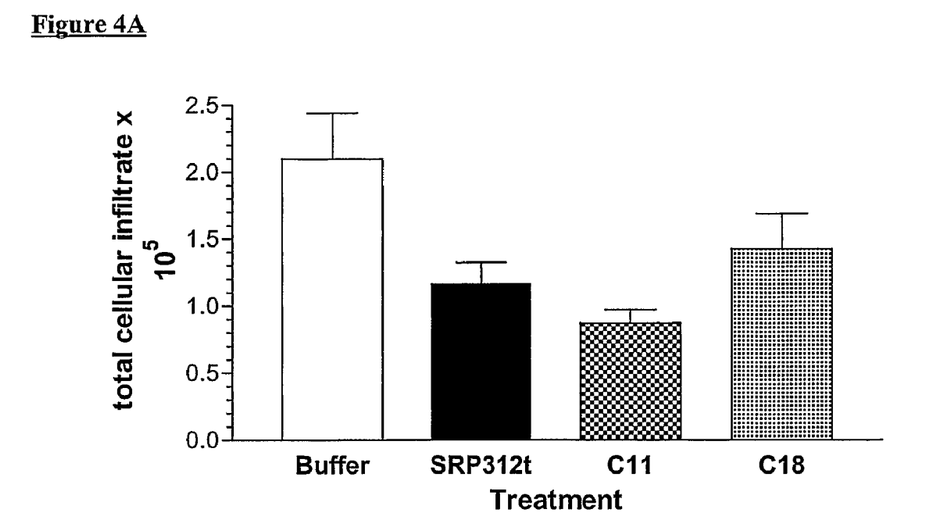
FIG. 4A shows results of total cellular infiltrate on administration of control, SRP312t, C11:1 10-11 and C18:1 10-11.

SRP312t is a C16:1 characterized by an unusual double bond at position 10-11. A number of synthetic variants were produced to determine the importance of chain length while maintaining the double bond at position 10-11. We compared whether the two synthetic variants C11:1 10-11 and C18:1 10-11 maintain the therapeutic properties of SRP312t. Mice were sensitized with ovalbumin in alum and treated with these synthetic variants. Allergic mice were then challenged with ovalbumin and the ensuing pulmonary inflammation quantified. We found that C11:1 10-11 and to a lesser extent C18:1 10-11 reduced the total cellular infiltrate in allergen challenged allergic mice (FIG. 4A).

Bond Position

SRP312t is a C16:1 characterized by an unusual double bond at position 10-11. A number of variants were synthetically produced or obtained commercially to determine the importance of the position of the double bond. We compared whether a commercially available lipid (C18:1 9-10) retains the therapeutic properties of SRP312t. Mice were sensitized with ovalbumin in alum and treated with this compound.

Figure 4B:
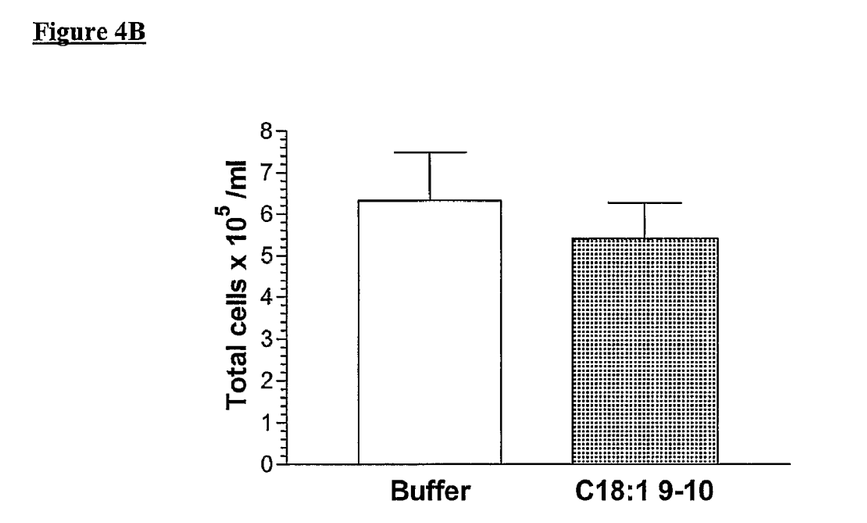
FIG. 4B compares results of total cellular infiltrate on administration of control and C18:1 9-10 TAG.

Allergic mice were then challenged with ovalbumin and the ensuing pulmonary inflammation quantified. We found that treatment with a C18:1 9-10 failed to reduce the total cellular infiltrate in allergen challenged allergic mice (FIG. 4B).

Figure 4C:
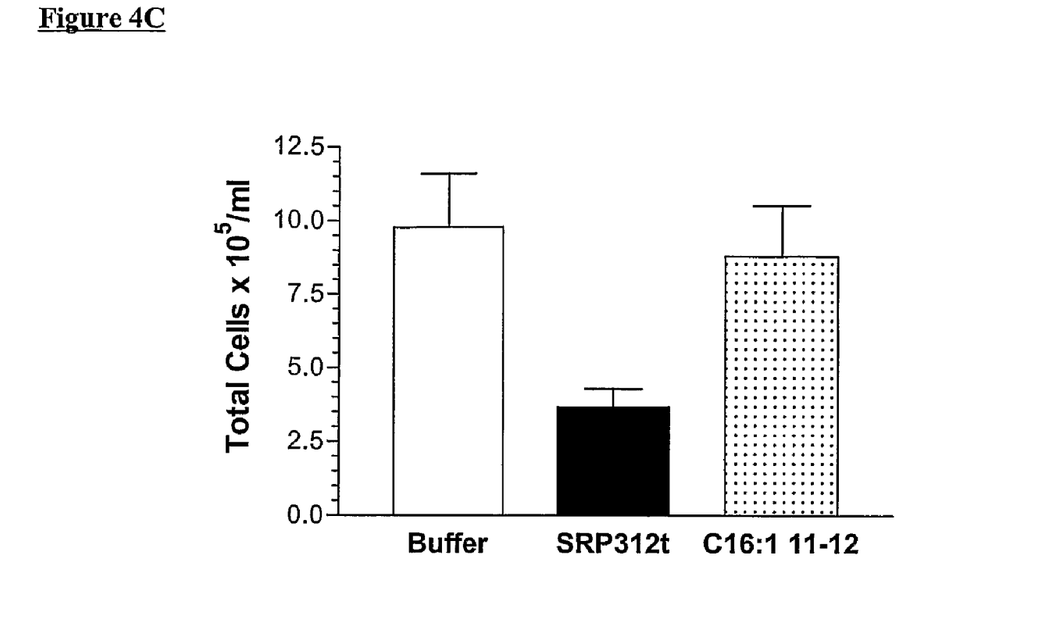
FIG. 4C compares results of total cellular infiltrate on administration of SRP312t and C16:1 11-12.

To assess the importance of the bond position in the compounds of the invention, a synthetic compound (C16:1 11-12) was prepared as described above. Activity of this compound was compared to SRP 312t (C16:1 10-11). Mice were sensitised with ovalbumin in alum and treated with SRP 312t and C16:1 11-12. Allergic mice were then challenged with ovalbumin and the ensuring pulmonary inflammation was quantified. Treatment with C16:1 11-12 failed to reduce the total cellular infiltrate in allergen challenged allergic mice (FIG. 4C).

Cis v Trans

Figure 4D:
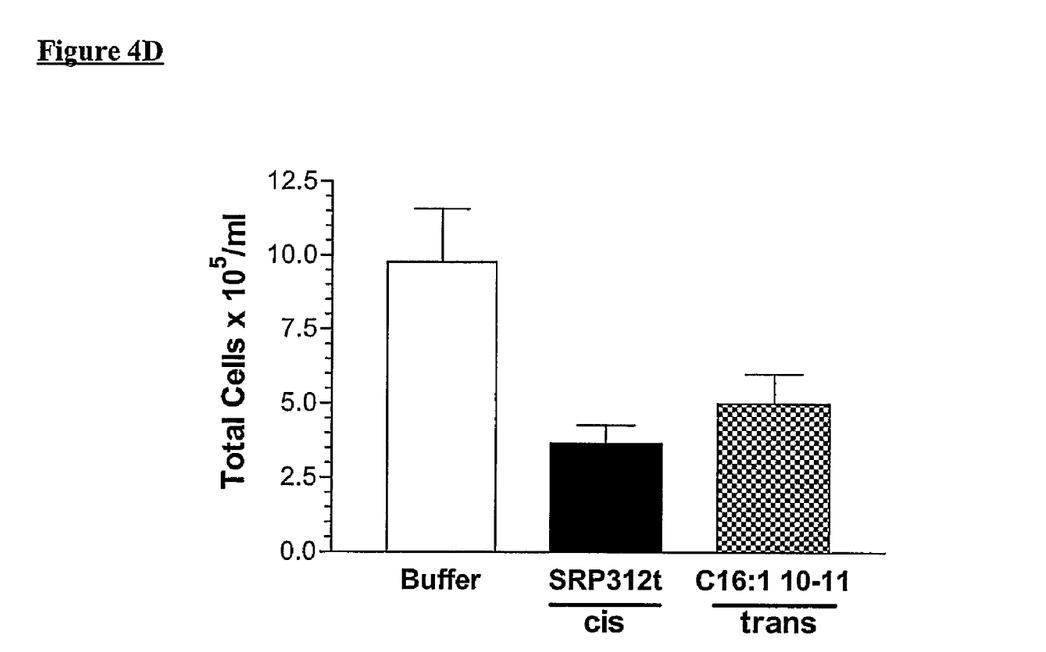
FIG. 4D compares results of total cellular infiltrate on administration of SRP312t and C16:1 10-11.

To determine whether changes from a cis to a trans molecule configuration affect the activity of SRP312t, we compared SRP312t (cis) with the synthetic variant C16:1 10-11 trans. Mice were sensitized with ovalbumin in alum and treated with the two compounds. Allergic mice were then challenged with ovalbumin and the ensuing pulmonary inflammation quantified. Both groups showed a reduction in the cellular infiltrate, although those receiving SRP312t showed a greater reduction (FIG. 4D).

The invention claimed is:

1. A compound which is a mono, di or tri-ester of 1,2,3-propanetriol, said ester comprising one, two or three fatty acids selected from the group consisting of C12, C14, C16, C20 or C24 fatty acids, wherein said fatty acids have at least one double bond, and wherein said fatty acid comprises said double bond at position C10-C11.

2. The compound of claim 1, wherein said fatty acid is a C12 fatty acid.

3. The compound of claim 1, wherein said fatty acid is a C14 fatty acid.

4. The compound of claim 1, wherein said fatty acid is a C16 fatty acid.

5. The compound of claim 1, wherein said fatty acid is a C20 fatty acid.

6. The compound of claim 1, wherein said fatty acid is a C24 fatty acid.

7. The compound of claim 1, wherein said C12, C14, C16, C20 or C24 fatty acid has only one double bond, said double bond occurring at position C10-C11.

8. The compound of claim 7, wherein said fatty acid having only one double bond is a C12 fatty acid.

9. The compound of claim 7, wherein said fatty acid having only one double bond is a C14 fatty acid.

10. The compound of claim 7, wherein said fatty acid having only one double bond is a C16 fatty acid.

11. The compound of claim 7, wherein said fatty acid having only one double bond is a C20 fatty acid.

12. The compound of claim 7, wherein said fatty acid having only one double bond is a C24 fatty acid.

13. The compound of claim 7, wherein said ester is a mono-ester of a C12 fatty acid.

14. The compound of claim 7, wherein said ester is a di-ester of a C12 fatty acid.

15. The compound of claim 7, wherein said ester is a tri-ester of a C12 fatty acid.

16. The compound of claim 7, wherein said ester is a mono-ester of a C14 fatty acid.

17. The compound of claim 7, wherein said ester is a di-ester of a C14 fatty acid.

18. The compound of claim 7, wherein said ester is a tri-ester of a C14 fatty acid.

19. The compound of claim 7, wherein said ester is a mono-ester of a C16 fatty acid.

20. The compound of claim 7, wherein said ester is a di-ester of a C16 fatty acid.

21. The compound of claim 7, wherein said ester is a tri-ester of a C16 fatty acid.

22. The compound of claim 7, wherein said ester is a mono-ester of a C20 fatty acid.

23. The compound of claim 7, wherein said ester is a di-ester of a C20 fatty acid.

24. The compound of claim 7, wherein said ester is a tri-ester of a C20 fatty acid.

25. The compound of claim 7, wherein said ester is a mono-ester of a C24 fatty acid.

26. The compound of claim 7, wherein said ester is a di-ester of a C24 fatty acid.

27. The compound of claim 7, wherein said ester is a tri-ester of a C24 fatty acid.

28. The compound of claim 1 wherein said double bond at position C10-C11 is cis.

29. The compound of claim 7 wherein said double bond at position C10-C11 is cis.

30. The compound of claim 1 wherein said double bond at position C10-C11 is trans.

31. The compound of claim 7 wherein said double bond at position C10-C11 is trans.

32. A method for treating an allergic disorder comprising the step of administering an effective amount of a mono, di or tri-ester of 1,2,3-propanetriol, said ester comprising one, two or three fatty acids, selected from C11 to C24 fatty acids, wherein said fatty acids have at least one double bond, wherein said fatty acid comprises said double bond at position C10-C11, and wherein said allergic disorder is selected from the group consisting of asthma, eczema, and hay fever.

33. The method of claim 32, wherein said allergic disorder is selected from the group consisting of asthma, eczema and hay fever.

34. The method of claim 33, wherein said fatty acid is a C11 fatty acid.

35. The method of claim 33, wherein said fatty acid is a C12 fatty acid.

36. The method of claim 33, wherein said fatty acid is a C14 fatty acid.

37. The method of claim 33, wherein said fatty acid is a C16 fatty acid.

38. The method of claim 33, wherein said fatty acid is a C18 fatty acid.

39. The method of claim 33, wherein said fatty acid is a C20 fatty acid.

40. The method of claim 33, wherein said fatty acid is a C22 fatty acid.

41. The method of claim 33, wherein said fatty acid is a C24 fatty acid.

42. The method of claim 33, wherein said C11 to C24 fatty acid has only one double bond, said double bond occurring at position C10-C11.

43. The method of claim 42, wherein said fatty acid having only one double bond is a C11 fatty acid.

44. The method of claim 42, wherein said fatty acid having only one double bond is a C12 fatty acid.

45. The method of claim 42, wherein said fatty acid having only one double bond is a C14 fatty acid.

46. The method of claim 42, wherein said fatty acid having only one double bond is a C16 fatty acid.

47. The method of claim 42, wherein said fatty acid having only one double bond is a C18 fatty acid.

48. The method of claim 42, wherein said fatty acid having only one double bond is a C20 fatty acid.

49. The method of claim 42, wherein said fatty acid having only one double bond is a C22 fatty acid.

50. The method of claim 42, wherein said fatty acid having only one double bond is a C24 fatty acid.

51. The method of claim 42, wherein said ester is a mono-ester of a C11 fatty acid.

52. The method of claim 42, wherein said ester is a di-ester of a C11 fatty acid.

53. The method of claim 42, wherein said ester is a tri-ester of a C11 fatty acid.

54. The method of claim 42, wherein said ester is a mono-ester of a C12 fatty acid.

55. The method of claim 42, wherein said ester is a di-ester of a C12 fatty acid.

56. The method of claim 42, wherein said ester is a tri-ester of a C12 fatty acid.

57. The method of claim 42, wherein said ester is a mono-ester of a C14 fatty acid.

58. The method of claim 42, wherein said ester is a di-ester of a C14 fatty acid.

59. The method of claim 42, wherein said ester is a tri-ester of a C14 fatty acid.

60. The method of claim 42, wherein said ester is a mono-ester of a C16 fatty acid.

61. The method of claim 42, wherein said ester is a di-ester of a C16 fatty acid.

62. The method of claim 42, wherein said ester is a tri-ester of a C16 fatty acid.

63. The method of claim 42, wherein said ester is a mono-ester of a C18 fatty acid.

64. The method of claim 42, wherein said ester is a di-ester of a C18 fatty acid.

65. The method of claim 42, wherein said ester is a tri-ester of a C18 fatty acid.

66. The method of claim 42, wherein said ester is a mono-ester of a C20 fatty acid.

67. The method of claim 42, wherein said ester is a di-ester of a C20 fatty acid.

68. The method of claim 42, wherein said ester is a tri-ester of a C20 fatty acid.

69. The method of claim 42, wherein said ester is a mono-ester of a C22 fatty acid.

70. The method of claim 42, wherein said ester is a di-ester of a C22 fatty acid.

71. The method of claim 42, wherein said ester is a tri-ester of a C22 fatty acid.

72. The method of claim 42, wherein said ester is a mono-ester of a C24 fatty acid.

73. The method of claim 42, wherein said ester is a di-ester of a C24 fatty acid.

74. The method of claim 42, wherein said ester is a tri-ester of a C24 fatty acid.

* * * * *